United States Patent [19]

Charpin et al.

[11] Patent Number: 5,164,185
[45] Date of Patent: Nov. 17, 1992

[54] PHARMACEUTICAL AND COSMETIC DEPIGMENTATION COMPOSITIONS WITH A CAFFEIC ACID BASE

[75] Inventors: Isabelle Charpin, St Maur Des Fosses; Didier Candau, Melun; Quang L. N'Guyen, Antony; Christiane Montastier, Maisons Laffitte; Francois Millecamps, Paris, all of France

[73] Assignee: L'Oreal, Paris, France

[21] Appl. No.: 691,045

[22] PCT Filed: Oct. 19, 1990

[86] PCT No.: PCT/FR90/00760
§ 371 Date: Aug. 13, 1991
§ 102(e) Date: Aug. 31, 1991

[87] PCT Pub. No.: WO91/05543
PCT Pub. Date: May 2, 1991

[30] Foreign Application Priority Data

Oct. 20, 1989 [FR] France .................. 89 13774

[51] Int. Cl.$^5$ ................................. A61K 7/135
[52] U.S. Cl. ........................ 424/401; 424/62
[58] Field of Search ............... 424/401, 62, 94.3; 514/852, 858

[56] References Cited

U.S. PATENT DOCUMENTS

| | | | |
|---|---|---|---|
| 3,982,999 | 9/1976 | Kharasch | 424/94.3 |
| 4,136,166 | 1/1979 | Barnett et al. | 424/62 |
| 4,767,750 | 8/1988 | Jacquet et al. | 514/852 |
| 4,824,865 | 4/1989 | Bowser et al. | 514/858 |
| 4,990,330 | 2/1991 | Oyama | 424/62 |

FOREIGN PATENT DOCUMENTS

| | | |
|---|---|---|
| 1533371 | 7/1968 | France . |
| 2613622 | 12/1978 | France . |
| 2390160 | 10/1988 | France . |
| 2-55607 | 10/1990 | Japan . |

OTHER PUBLICATIONS

Patent Abstracts of Japan, vol. 11, No. 349 (C-456)(2796), Nov. 14, 1987.
Patent Abstract of Japan, vol. 6, No. 44, (C-95)(922), Mar. 19, 1982.

*Primary Examiner*—Thurman K. Page
*Assistant Examiner*—D. Colucci
*Attorney, Agent, or Firm*—Cushman, Darby & Cushman

[57] ABSTRACT

A pharmaceutical or cosmetic depigmenting composition for application to the skin so as to improve the aesthetic appearance of the skin or to treat pathological or accidental hyperpigmentation contains caffeic acid or an ester or amide thereof in an amount effective to depigment the skin.

19 Claims, 5 Drawing Sheets

FIG.1

PHARMACEUTICAL AND COSMETIC DEPIGMENTATION COMPOSITIONS WITH A CAFFEIC ACID BASE

The present invention relates to a pharmaceutical or cosmetic depigmenting composition which contains, as an active ingredient, caffeic acid or one of its derivatives.

It will be remembered that the mechanism which forms skin pigmentation, i.e., the formation of melanins, is especially complex and involves the triggering of the main steps diagrammed below:

TYROSINE→DOPA→DOPAQUINONE→DOPACHROME→MELANINS tyrosinase being the main enzyme involved in this series of reactions.

The depigmenting agents currently used in cosmetology are, more specifically, phenolic derivatives, and, most notably, hydroquinone or a hydroquinone ether such as hydroquinone monomethyl ether.

While these compounds have a certain level of effectiveness, they are not, unfortunately, free from side effects that make their use a sensitive, and even dangerous, matter.

Thus, hydroquinone, whose use is restricted, moreover, to a 2% concentration, is especially irritating and cytotoxic for melanocytes. Many authors have contemplated its total or partial replacement.

Thus, French Patent No. 87.08236 (2,616,325) proposed a composition containing a combination of hydroquinone and kojic acid or of its derivatives, in particular its salts and esters.

International Application WO 85/0401 proposes, in addition and for the same purpose, a depigmenting composition containing a combination of hydroquinone or its benzylic monoether and salicylic acid.

Moreover, among the compositions producing a pronounced depigmenting action, mention must also be made of the Kligman trio, generally chosen as the compound of reference, which is based on a combination of acidic Vitamin A, hydroquinone, and a steroid, either dexamethasone or hydrocortisone. The use of this composition has, however, been restricted to the extent that it exhibits a high level of irritation caused by acidic Vitamin A as well as undesirable effects caused by hypervitaminosis A.

It has now been well established that a substance produces a depigmenting action if it acts directly on the vitality of the epidermal melanocytes where melanogenesis normally takes place, and/or if it interferes with one of the stages of melanin biosynthesis, either by inhibiting one of the enzymes involved or by its insertion as a structural analogue in the synthesis pathway, which can thus become blocked, thereby producing the depigmenting effect.

The use of harmless topical depigmenting substances exhibiting a high degree of efficacy is most especially sought in order to treat regional hyperpigmentation caused by melanocytic hyperactivity, such as idiopathic melasmas occurring during pregnancy ("mask of pregnancy" or chloasma) or melasmas secondary to estrogen-progesterone contraception, cases of localized hyperpigmentation caused by hyperactivity and benign melanocytic proliferation, such as senile pigmentary spots, termed actinic lentigos, accidental hyperpigmentation such as photosensitization and post-lesion scarring, as well as certain leucodermas such as vitiligo, in which, because pigmentation cannot be restored to the injured skin, the areas of remaining normal skin are depigmented so as to impart to the total skin area a homogeneous white color.

Following various studies conducted on numerous substances used either singly or in combination, it was found, surprisingly and unexpectedly, that caffeic acid or its derivatives, and especially its esters and amides, produced an especially interesting depigmenting action, their efficacy being mainly the result of an inhibition of tyrosinasic activity leading to the limited formation of dopachrome and thus, of melanins.

This new property of caffeic acid and its derivatives had heretofore never been brought to light, despite the many studies conducted on this acid.

Therefore, the present invention relates to a pharmaceutical or cosmetic depigmenting composition used in a topical application and containing, in a vehicle suitable for such an application, an effective quantity of caffeic acid or of one of its esters or amides.

Among the esters of caffeic acid, mention may be made especially of the compounds corresponding to the formula:

(1)

R representing an alkyl radical of from 1 to 8 carbon atoms, and preferably the methyl radical.

Among the caffeic acid amides, mention may be made, in particular, of the compounds corresponding to the formula:

(2)

R' representing an alkyl radical of from 1 to 8 carbon atoms, and preferably an alkyl of from 6 to 8 carbon atoms. The amide having 6 carbon atoms is most especially preferred.

In composition s according to the invention, the concentration of caffeic acid or of one of its derivatives generally ranges between 0.1 and 8%, and preferably between 1 and 3% by weight.

The vehicle for the compositions according to the invention may be, in particular, an aqueous or hydroalcoholic solution, an oil-in-water or water-in-oil emulsion, an emulsified gel, or a diphase system.

The compositions according to the invention preferably exist as lotions, creams, gels, masks, microspheres or nanospheres, or vesicular dispersions. In these latter, at least one of the active ingredients may be liposomes. Moreover, it was discovered, surprisingly, that when caffeic acid or one of its derivatives was associated with a substance chosen from among the following: hydroquinone or one of its ethers, kojic acid (hydroxy-5 hydroxymethyl-2 H-4 pyranone-4), a water-soluble copper salt, or a mixture of these substances, increased efficacy of the depigmenting action was observed, and this action could be attributed only to a synergistic effect.

When the compositions according to the invention contain hydroquinone or a hydroquinone ether such as hydroquinone monomethyl ether, the concentration generally ranges between 0.2 and 6%, but preferably between 0.2 and 2% by weight, in order to prevent side effects.

When the compositions contain kojic acid, the concentration generally ranges between 0.1 and 3% by weight, and preferably between 0.5 and 2%.

When the composition contain a water-soluble copper salt, this latter exists in a molar Cu II concentration equivalent to that of caffeic acid or its derivatives. These salts include, in particular, copper gluconate or sulfate, but preferably copper gluconate in a concentration of between 0.2 and 20% by weight and preferably between 2.5 and 7.5%.

According to one preferred embodiment, a keratolytic agent is included additionally in the composition in a concentration, for example, of between 0.5 and 10% by weight, and preferably between 1 and 3%.

This keratolytic agent may include, in particular, urea or a carboxylic hydroxyacid, such as glycolic, or preferably salicylic, acid or its derivatives, and in particular, n-octanoyl-5 salicylic acid.

In accordance with the invention, the depigmenting composition may therefore be of the binary, ternary, quaternary type.

The combinations falling within the scope of the invention include most notably the following:

caffeic acid + kojic acid + salicylic acid or one of its derivatives;
caffeic acid + kojic acid + hydroquinone;
caffeic acid + kojic acid + copper gluconate;
caffeic acid + kojic acid + hydroquinone + copper gluconate;
caffeic acid + hydroquinone;
caffeic acid + hydroquinone + copper gluconate;
caffeic acid + copper gluconate;
caffeic acid + kojic acid, the first four being especially preferred.

The invention also relates to a procedure for the preparation of the compositions described above, in which, using conventional methods, the ingredient or ingredients are mixed with the vehicle and any other ingredients that may be added.

The present invention also relates to the use of caffeic acid (or of one of its esters or amides), possibly in combination with the other above-mentioned ingredients, as the active ingredient in the preparation of a cosmetic or pharmaceutical depigmenting composition.

The compositions according to the invention may of course contain other ingredients commonly used in cosmetology or dermatological pharmacology, such as moistening agents, preserving agents, coloring agents, perfumes, penetration agents such as diethylene glycol monoethyl ether, etc.

These compositions are applied topically in humans, in quantities corresponding to the normal application doses of the type of composition in question (gel, cream, lotion, etc.). For example, in the case of a cream, from 0.5 to 3 mg, and preferably from 1 to 2 mg of cream are used per cm$^2$ of skin per application, at the rate of one or two applications daily.

"IN VITRO" STUDY

The efficacy of the various combination according to the invention have been studied in vitro by measuring out, using visible spectrophotometry (475 nm), the quantity of dopachrome formed during the chain of tyrosine-oxidation reactions. These oxidation reactions are catalyzed in vitro using fungus-derived tyrosinase in the presence of a co-substrate (for example, a small quantity of L-dopa) in order to trigger the hydroxylation reaction of L-tyrosine into L-dopa, this latter being then oxidized by catalysis into dopaquinone, then into dopachrome, an intermediate product formed before the non-enzymatic oxidation reactions leading to melanin formation.

Accordingly, the concentration of dopachrome formed over time is monitored in the presence of various inhibitors of tyrosinasic activity.

The concentrations of inhibitors are expressed as molar percents in relation to the concentration of tyrosine present in the reactive medium.

The inhibitory effect may be expressed, in relation to the control curve (absence of inhibitor) by lowering of the quantity of dopachrome formed and/or by a slowing of dopachrome-formation kinetics.

In the first case, this lowering signifies a reduction of the maximum level of optical density reached (the case of active products which tend to be limiters of formed dopachrome), and, in the second case, by a reduction of the slope tangent to the origin (the case of active products which impede dopachrome formation).

BRIEF DESCRIPTION OF THE DRAWINGS

The curves in FIGS. 1 to 5 illustrate the inhibitor effect of the various substances and substance combination according to the invention.

EXPERIMENTAL RECORD

Reagents

Figure 1:
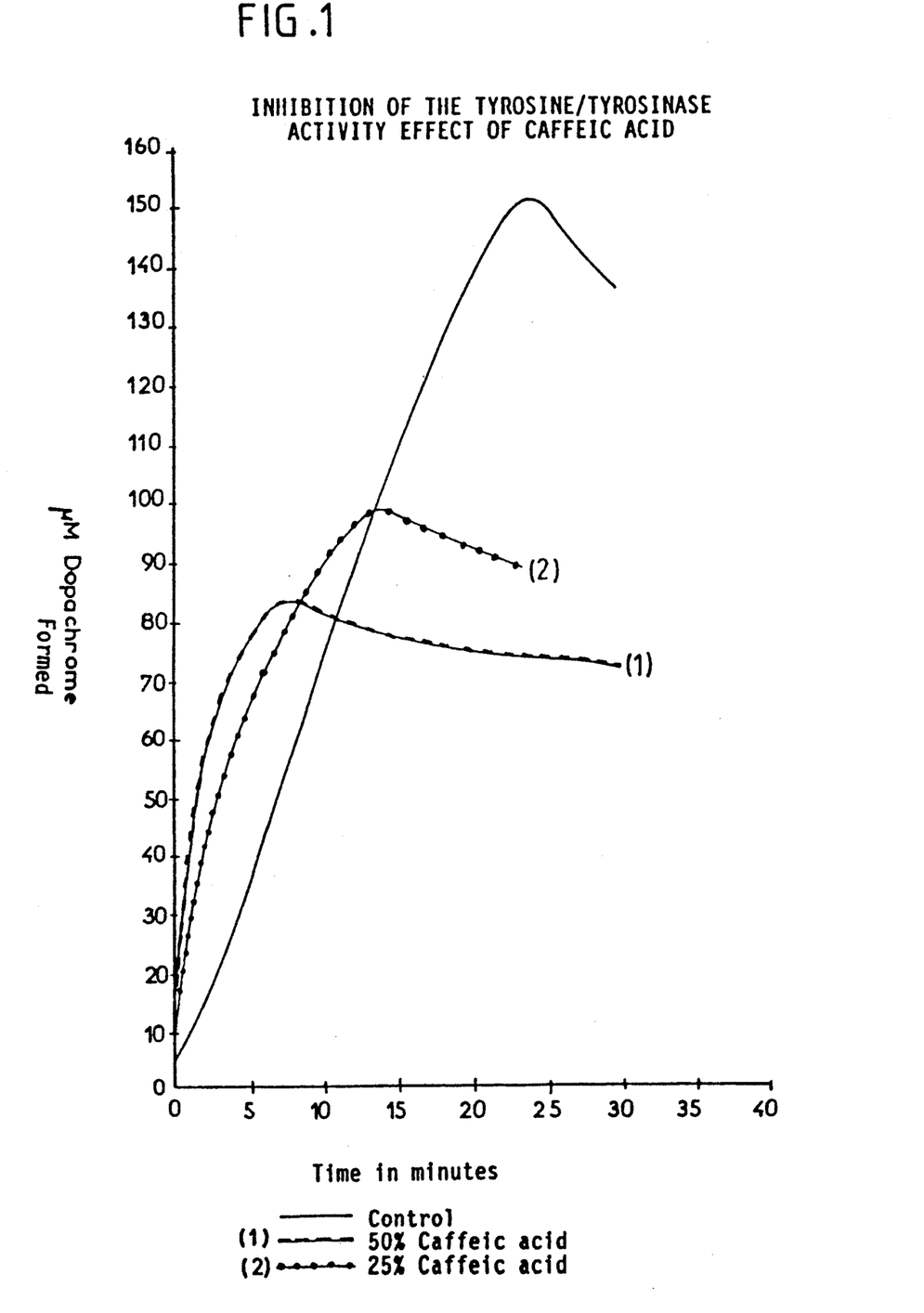
Figure 2:
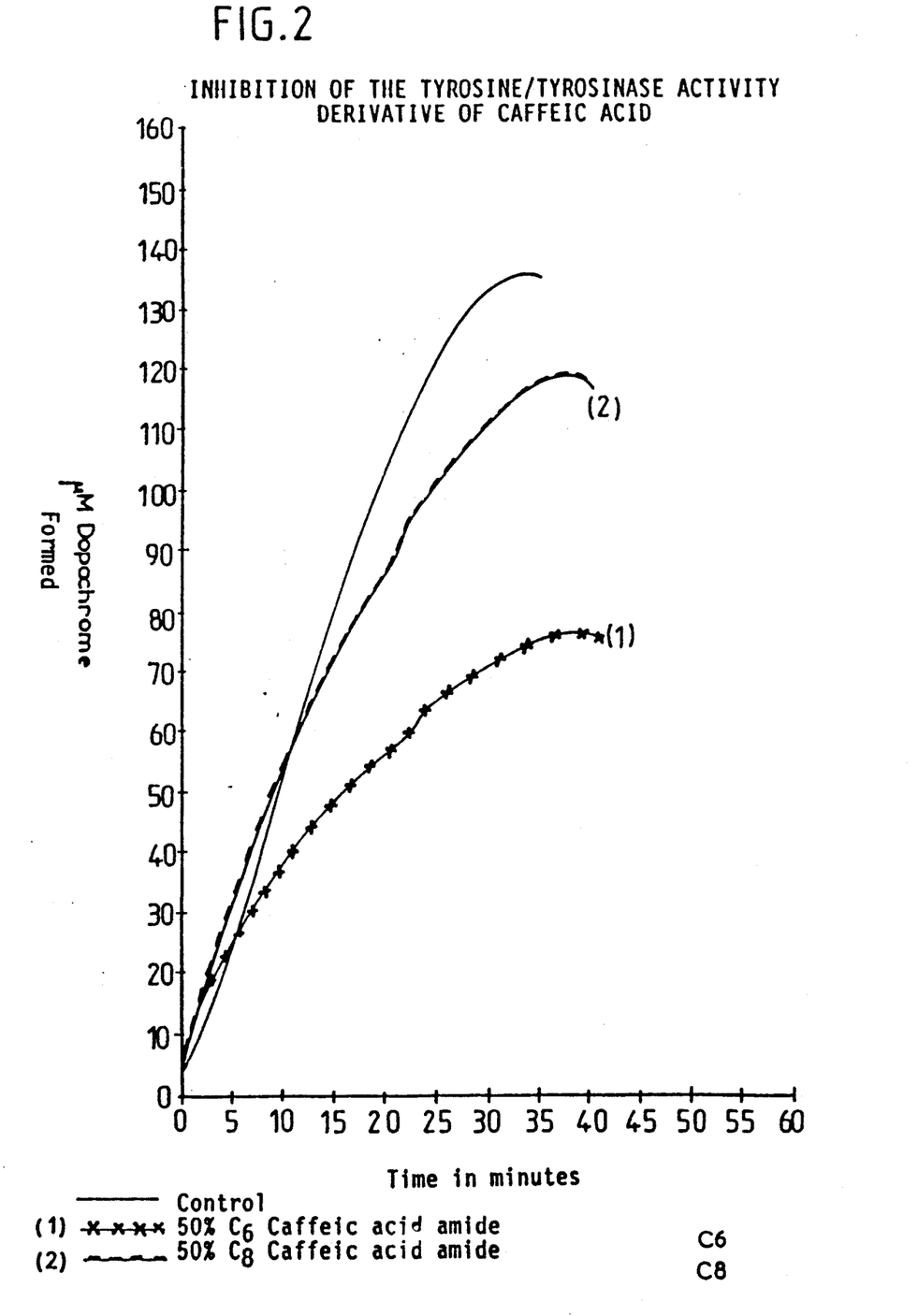
Figure 3:
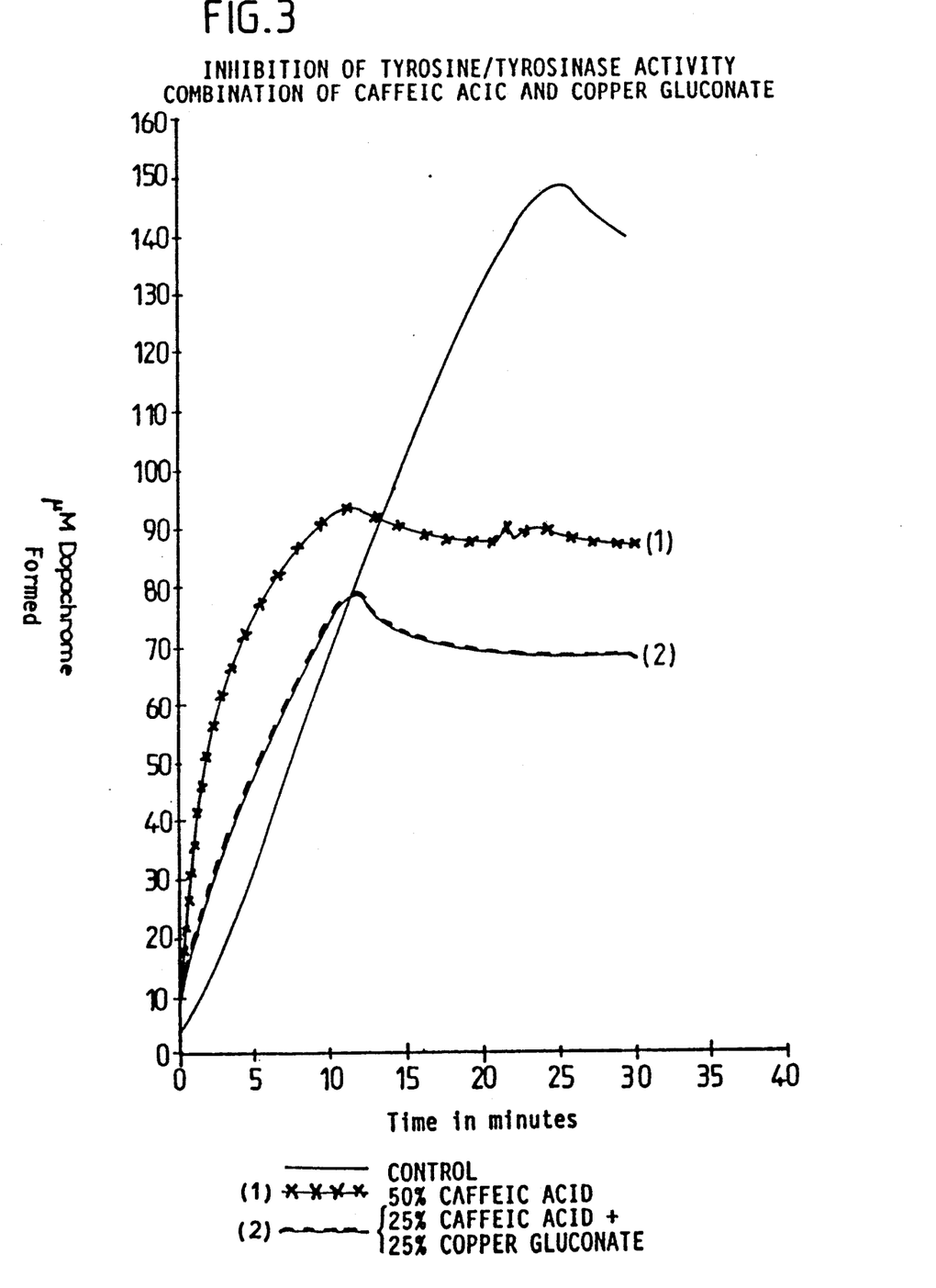
Figure 4:
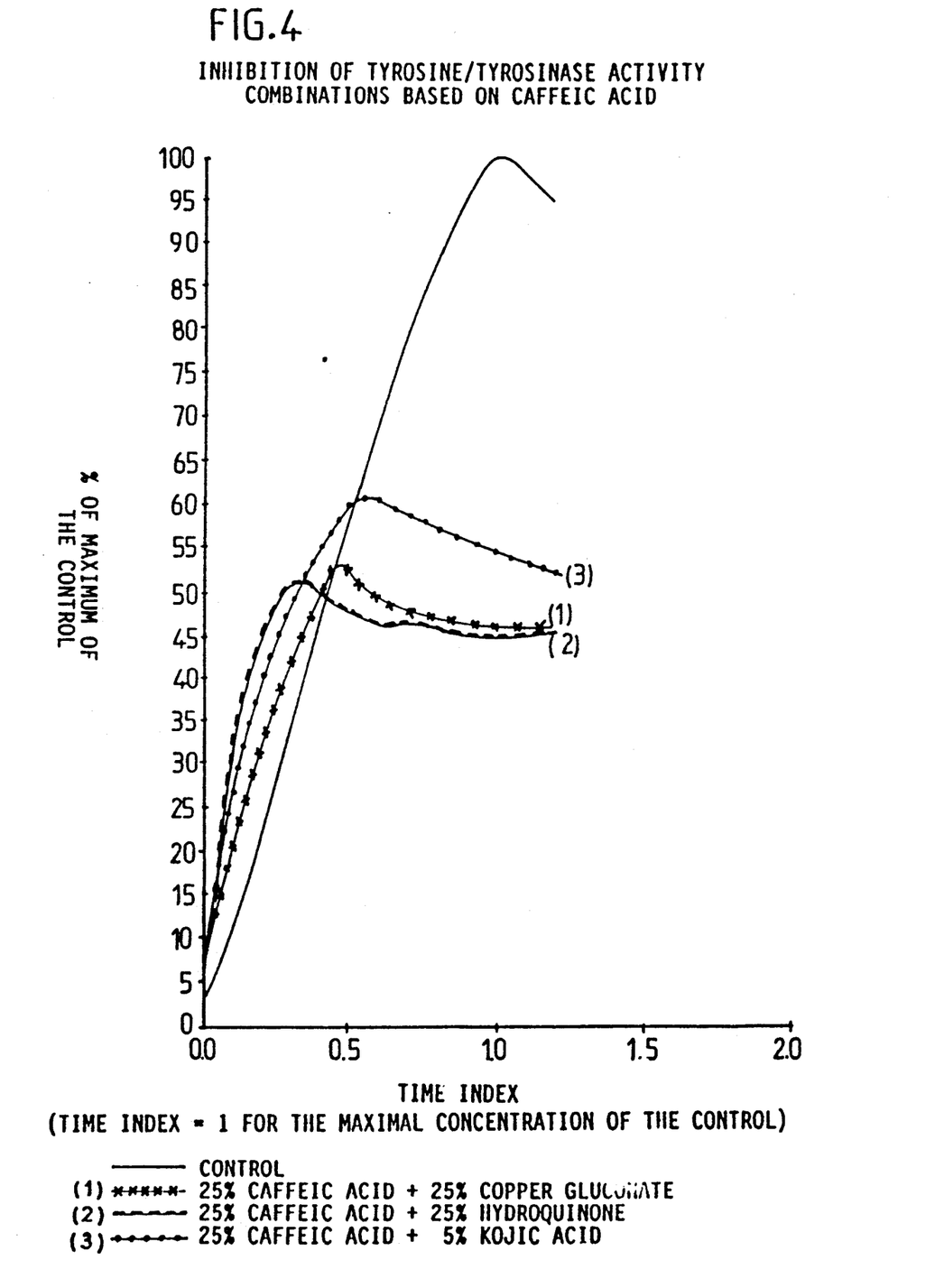
Figure 5:
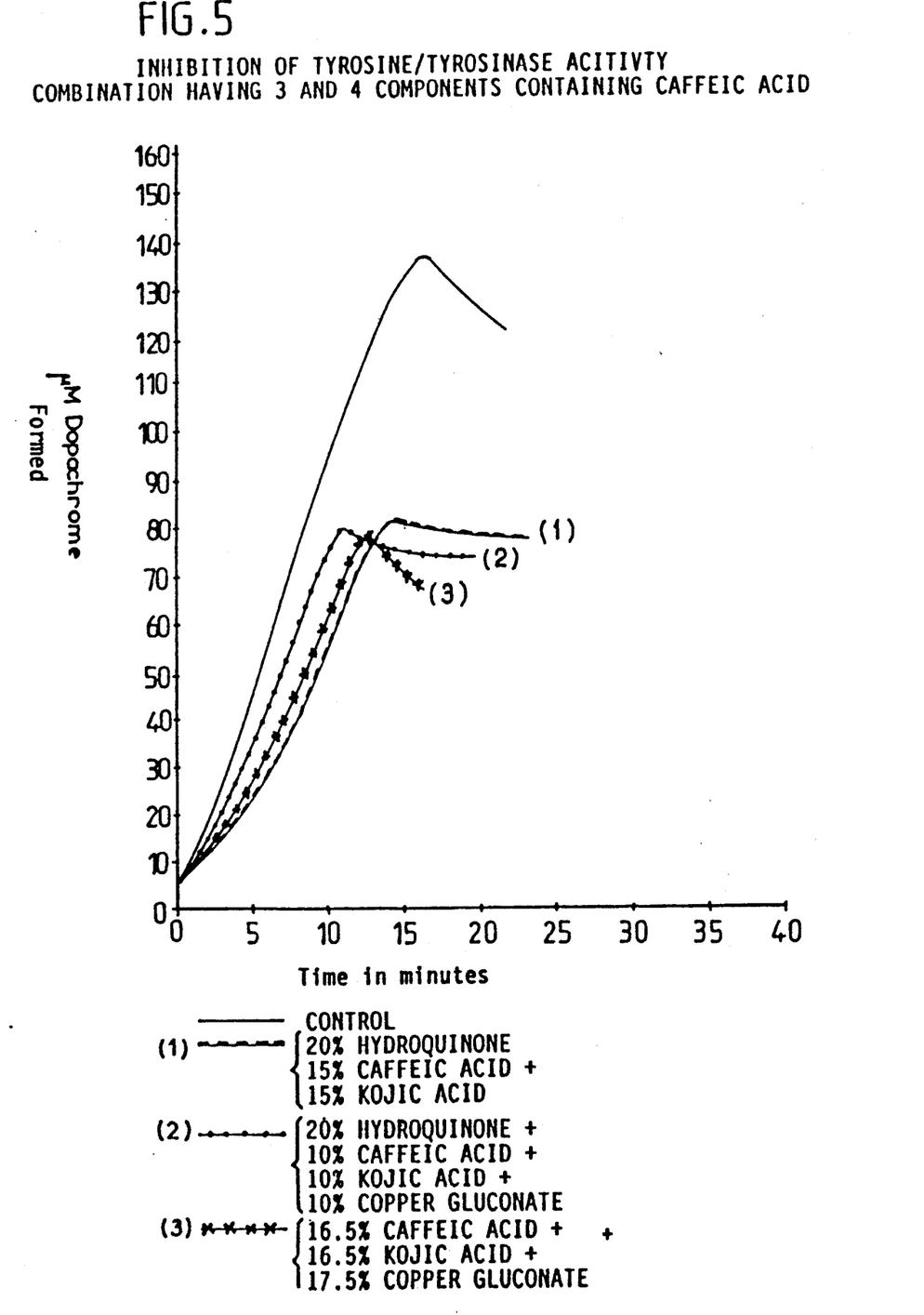

A—Phosphate buffer of 0.1M pH=6.5
B—Parent solution of L-tyrosine at $2,10^{-3}$M in A
C—Parent solution of L-dopa at $10^{-4}$M in A
D—Parent solution of fungus-derived tyrosinase at 2,400 units/ml in A
E—Parent solution of the inhibitor at $10^{-2}$M in A (Solutions C and D are to be prepared on the same day.)

Measurements

Reference cell:
 3 ml of A
Test cell:
 1 ml of B
 0.1 ml of C
 1 85 ml of A+E
Homogenize and equilibrate at 25° C.
Add 0.05 ml of D
Mix rapidly and trigger absorption kinetics at 475 nm.

There are provided, for purposes of illustration and without limiting the scope of the invention, several examples of the depigmenting compositions according to the invention:

EXAMPLE 1

Depigmenting Cream

| | |
|---|---|
| Caffeic acid | 1.27% |
| Kojic acid | 1% |

| | |
|---|---|
| N-octanoyl-5-salicylic acid | 2% |
| Triethanolamine | 1.3% |
| Jojoba oil | 3% |
| Mixture of ethyl-2 ketostearyl hexanoate and isopropyl myristate | 3% |
| Hydrogenated isoparaffin | 3% |
| Stearic acid | 2% |
| Ketostearylic alcohol | 1.5% |
| Isopropyl myristate | 3% |
| Preserving agent | 0.4% |
| Buffer | 0.71% |
| Disodium salt of hydrated ethylene diaminotetracetic acid (2 H$_2$O) | 0.1% |
| UVA-UVB filters | 2% |
| Perfume | 0.4% |
| Carboxyvinyl polymer | 0.6% |
| Diethylene glycol monoethyl ether | 7.5% |
| Sterile demineralized water | 58.22% |
| Polyethylene glycol stearate | 3% |
| Mixture of glyceryl monostearate and polyethylene glycol stearate | 3% |
| Mixture of ketylstearylic alcohol and oxyethylene-containing ketylstearylic alcohol | 3% |

This cream was clinically tested on a group of 21 subjects between 45 and 65 years old having age spots on their hands.

The treatment, which lasted two months, consisted in a twice-daily application on one hand, the other hand serving as a control. 2 mg of cream per cm$^2$ of skin was used for each application.

At the end of the treatment, a quantitative evaluation was conducted using a CR 200 chromometer (Minolta) on the treated and untreated spots.

The absolute color variation, which did not distinguish among any shades, between the time T=0 and T=2 months was computed as follows:

$$\Delta E = \sqrt{\Delta L^2 + \Delta a^2 + \Delta b^2} ,$$

L, a, and b being the coordinates which delimit the colorimetric space used (Δ signifies: change in).

The results are as follows:-

| | Treated hand | Untreated hand |
|---|---|---|
| ΔE | 2.31 | 2.8 |
| % inhibition when compared to the untreated hand | 21.6 | |

The subjective efficacy of this cream is 60%. The tolerance is 100%.

EXAMPLE 2

Depigmenting Cream

| | |
|---|---|
| Caffeic acid | 1.27% |
| Kojic acid | 1% |
| Hydroquinone | 2% |
| Triethanolamine | 1.3% |
| Jojoba oil | 3% |
| Mixture of ethyl-2 ketostearyl hexanoate and isopropyl myristate | 3% |
| Hydrogenated isoparaffin | 3% |
| Stearic acid | 2% |
| Ketostearylic alcohol | 1.5% |
| Isopropyl myristate | 3% |
| Preserving agent | 0.4% |
| Buffer | 0.71% |
| Disodium salt of hydrated ethylene diaminotetracetic acid (2 H$_2$O) | 0.1% |
| UVA-UVB filters | 2% |
| Perfume | 0.4% |
| Carboxyvinyl polymer | 0.6% |
| Diethylene glycol monoethyl ether | 7.5% |
| Sterile demineralized water | 58.22% |
| Polyethylene glycol stearate | 3% |
| Mixture of glyceryl monostearate and polyethylene glycol stearate | 3% |
| Mixture of ketylstearylic alcohol and oxyethylene-containing ketylstearylic alcohol | 3% |

EXAMPLE 3

Depigmenting Cream

| | |
|---|---|
| Caffeic acid | 1.27% |
| Hydroquinone | 2% |
| Triethanolamine | 1.3% |
| Jojoba oil | 3% |
| Mixture of ethyl-2 ketostearyl hexanoate and isopropyl myristate | 3% |
| Hydrogenated isoparaffin | 3% |
| Stearic acid | 2% |
| Isopropyl myristate | 3% |
| Ketylstearylic alcohol | 1.5% |
| Preserving agent | 0.4% |
| Buffer | 0.71% |
| Disodium salt of hydrated ethylene diaminotetracetic acid (2 H$_2$O) | 0.1% |
| UVA-UVB filters | 2% |
| Perfume | 0.4% |
| Carboxyvinyl polymer | 0.6% |
| Diethylene glycol monoethyl ether | 7.5% |
| Sterile demineralized water | 61.22% |
| Polyethylene glycol stearate | 3% |
| Mixture of glyceryl monostearate and polyethylene glycol stearate | 3% |
| Mixture of ketylstearylic alcohol and oxyethylene-containing ketylstearylic alcohol | 1% |

EXAMPLE 4

Depigmenting Lotion

| | |
|---|---|
| Caffeic acid | 2.35% |
| Hydroquinone | 2% |
| Copper gluconate | 6% |
| Buffer | 0.3% |
| Disodium salt of hydrated ethylene diaminotetracetic acid (2 H$_2$O) | 4.1% |
| Ethylene diaminotetramethylene phosphonic acid | 0.1% |
| Dimethylsulfoxide | 42.8% |
| Sterile demineralized water | 42.35% |

EXAMPLE 5

Depigmenting Lotion

| | |
|---|---|
| Caffeic acid | 1.6% |
| Kojic acid | 1.25% |
| Hydroquinone | 2% |
| Copper gluconate | 4% |
| Ethylene diaminotetramethylene phosphonic acid | 0.1% |
| Buffer | 0.3% |
| Disodium salt of hydrated ethylene diaminotetracetic acid (2 H$_2$O) | 3.3% |
| Dimethylsulfoxide | 43.9% |

-continued

| | |
|---|---|
| Sterile demineralized water | 43.55% |

EXAMPLE 6

Depigmenting Lotion

| | |
|---|---|
| Caffeic acid | 2.5% |
| Kojic acid | 2% |
| Copper gluconate | 6.5% |
| Buffer | 0.3% |
| Disodium salt of hydrated ethylene diaminotetracetic acid (2 H$_2$O) | 5.6% |
| Ethylene diaminotetramethylene phosphonic acid | 0.1% |
| Dimethylsulfoxide | 41.6% |
| Sterile demineralized water | 41.4% |

EXAMPLE 7

Depigmenting Lotion

| | |
|---|---|
| Caffeic acid | 8% |
| Buffer | 0.15% |
| Ethylene diaminotetramethylene phosphonic acid | 0.1% |
| Dimethylsulfoxide | 68.8% |
| Sterile demineralized water | 22.95% |

EXAMPLE 8

A vesicular dispersion is prepared according to the invention as a cream by implementing the following procedure:

The following products are added to a beaker:

| | |
|---|---|
| Non-ionic amphiphilic lipid corresponding to the formula: | 3.75 g |

$$RO + C_3H_5(OH)O \frac{}{n} H$$

in which: C$_3$H$_5$(OH)O]— represents one or a mixture of the following structures:

$$-CH_2-CHO- \text{ and/or } -CH-CH_2O-$$
$$\quad\quad | \quad\quad\quad\quad\quad\quad\quad\quad |$$
$$\quad\quad CH_2OH \quad\quad\quad\quad\quad CH_2OH$$

R being a hexadecyl radical and n̄ having a mean statistic value of 3

| | |
|---|---|
| Cholesterol | 3.75 g |

These two products are mixed by heating at a temperature of 100° C. in a nitrogen atmosphere, then the temperature of the melted mixture is reduced to 90° C. Then,

| | |
|---|---|
| n-octanoyl-5-salicyclic acid | 0.5 g | is added to this mixture.

After homogenization of the mixture, the following products are added:

| | |
|---|---|
| Glycerine | 3.0 g |
| Demineralized water | 19.3 g |

The mixture is next homogenized at a temperature of 70° C. using a VIRTIS-type ultradispersing machine. Next,

| | |
|---|---|
| Kojic acid | 1.0 g |
| Demineralized water | 23.02 g | are added.

After homogenization of the mixture using an ultradispersing machine at a temperature of 40° C.,

| | |
|---|---|
| Caffeic acid | 1.27 g |
| Diethylene glycol monoethyl ether | 7.5 g | are added, and then the mixture is homogenized once again at the same temperature.

Thus, a dispersion of lipidic vesicles, having an average size of approximately 0.2 micron, is obtained.

After bringing the temperature down to 25° C., the following are added:

| | |
|---|---|
| Vaseline oil | 14 g |
| Volatile silicon oil | 10 g. |

The mixture is homogenized using the ultradispersing machine, and finally, the following products are added:

| | |
|---|---|
| Perfume | 0.4 g |
| Carboxyvinyl polymer sold under the name "CARBOPOL 940" by the Goodrich company | 0.4 g |
| Triethanolamine | 1.5 g |
| Methyl parahydroxybenzoate | 0.2 g |
| Demineralized water | 10.41 g. |

A beige cream is thus obtained.

EXAMPLE 9

In accordance with the invention, a vesicular dispersion is prepared as a cream by proceeding as follows:

| | |
|---|---|
| Non-ionic amphiphilic lipid corresponding to the formula: | 3.75 g |

$$RO + C_3H_5(OH)O \frac{}{n} H$$

in which: C$_3$H$_5$(OH)O]— represents one or a mixture of the following structures:

$$-CH_2-CHO- \text{ and/or } -CH-CH_2O-$$
$$\quad\quad | \quad\quad\quad\quad\quad\quad\quad\quad |$$
$$\quad\quad CH_2OH \quad\quad\quad\quad\quad CH_2OH$$

R being a hexadecyl radical and n having a mean statistic value of 3

| | |
|---|---|
| Cholesterol | 3.75 g |

These two products are mixed by heating at a temperature of 100° C. in a nitrogen atmosphere, then the temperature of the melted mixture is reduced to 90° C. Then,

| | |
|---|---|
| n-octanoyl-salicyclic acid | 0.5 g | is added to this mixture.

After homogenization of the mixture, the following products are added:

| | |
|---|---|
| Glycerine | 3.0 g |
| Demineralized water | 14.5 g |

The mixture is then homogenized at a temperature of 70° C. using a VIRTIS-type ultradispersing machine. Next,

| | |
|---|---|
| Hydroquinone | 2 g |
| Sodium metabisulfite | 0.17 g |
| Sodium sulfite | 0.27 g |
| Citric acid | 0.2 g |
| Demineralized water | 26.12 g | are added.

After homogenization of the mixture using an ultradispersing machine at a temperature of 40° C.,

| | |
|---|---|
| Caffeic acid | 1.27 g |
| Diethylene glycol monoethyl ether | 7.5 g | are added, and then the mixture is homogenized once again at the same temperature.

Thus, a dispersion of lipidic vesicles, having an average size of approximately 0.2 micron, is obtained.

After bringing the temperature down to 25° C., the following are added:

| | |
|---|---|
| Vaseline oil | 14 g |
| Volatile silicon oil | 10 g. |

The mixture is homogenized using the ultradispersing machine, and finally, the following products are added:

| | |
|---|---|
| Perfume | 0.4 g |
| Carboxyvinyl polymer sold under the name "CARBOPOL 940" by the Goodrich company | 0.4 g |
| Triethanolamine | 1.4 g |
| Methyl parahydroxybenzoate | 0.2 g |
| Demineralized water | 10.51 g. |

A beige cream is thus obtained.

I claim:

1. A pharmaceutical or cosmetic depigmenting composition for application to the skin comprising, in a pharmaceutically or cosmetically acceptable vehicle for application to the skin, caffeic acid or an ester or amide thereof in an amount effective to depigment said skin.

2. The composition of claim 1 wherein said caffeic acid or an ester or amide thereof is present in an amount ranging from 0.1 to 8 percent by weight based on the total weight of said composition.

3. The composition of claim 1 wherein the ester of caffeic acid has the formula wherein R represents $C_1-C_8$ alkyl.

4. The composition of claim 1 wherein the amide of caffeic acid has the formula wherein R' represents $C_1-C_8$ alkyl.

5. The composition of claim 1 which also contains a substance selected from hydroquinone, hydroquinone ether, kojic acid, a water-soluble copper salt or a mixture thereof.

6. The composition of claim 1 which also contains hydroquinone or hydroquinone ether in an amount ranging from 0.2 to 6 percent by weight based on the total weight of said composition.

7. The composition of claim 1 which also contains kojic acid in an amount ranging from 0.1 to 3 percent by weight based on the total weight of said composition.

8. The composition of claim 1 which also contains a water-soluble copper salt in a molar concentration equivalent to that of said caffeic acid or an ester or amide thereof.

9. The composition of claim 8 wherein said water-soluble copper salt is copper gluconate.

10. The composition of claim 1 which also contains a keratolytic agent.

11. The composition of claim 10 wherein said keratolytic agent is urea or a hydroxylated carboxylic acid.

12. The composition of claim 11 wherein said hydroxylated carboxylic acid is salicylic acid, a salicylic acid derivative or glycolic acid.

13. The composition of claim 12 wherein said salicylic acid derivative is n-octanoyl-5-salicylic acid.

14. The composition of claim 10 wherein said keratolytic agent is present in an amount ranging from 0.5 to 10 percent by weight based on the total weight of said composition.

15. The composition of claim 1 which contains a combination of caffeic acid, kojic acid and n-octanoyl-5-salicylic acid.

16. The composition of claim 1 in the form of a lotion, a cream, a milk, a gel, a mask, microspheres, nanospheres or vesicular dispersions.

17. The composition of claim 1 which also contains at least one of a moistening agent, a preservative, a coloring agent, a perfume and a penetration agent.

18. A cosmetic treatment process for improving the aesthetic appearance of the skin comprising applying to the skin in an amount effective to improve the aesthetic appearance of the skin the composition of claim 1.

19. A pharmaceutical treatment process for the treatment of pathological or accidental hyperpigmentation comprising applying to the skin in an amount effective to treat pathological or accidental hyperpigmentation the composition of claim 1.

* * * * *